United States Patent
Blank et al.

(10) Patent No.: US 10,352,896 B2
(45) Date of Patent: Jul. 16, 2019

(54) COULOMETRIC TITRATION CELL

(71) Applicant: Mettler-Toledo GmbH, Greifensee (CH)

(72) Inventors: Thomas Blank, Schwerzenbach (CH); Günter Pfuhl, Schwerzenbach (CH); Félix Bécheiraz, Bülach (CH)

(73) Assignee: METTLER-TOLEDO GMBH, Greifensee (CH)

( * ) Notice: Subject to any disclaimer, the term of this patent is extended or adjusted under 35 U.S.C. 154(b) by 578 days.

(21) Appl. No.: 15/046,083

(22) Filed: Feb. 17, 2016

(65) Prior Publication Data
US 2016/0161447 A1 Jun. 9, 2016

Related U.S. Application Data

(63) Continuation of application No. PCT/EP2014/066953, filed on Aug. 7, 2014.

(30) Foreign Application Priority Data

Aug. 19, 2013 (EP) .................................... 13180899

(51) Int. Cl.
*G01N 27/447* (2006.01)
*G01N 31/16* (2006.01)
*G01N 27/44* (2006.01)

(52) U.S. Cl.
CPC ....... *G01N 27/44704* (2013.01); *G01N 27/44* (2013.01); *G01N 27/44756* (2013.01); *G01N 31/164* (2013.01)

(58) Field of Classification Search
CPC ...... G01N 27/423; G01N 27/42–27/44; G01N 27/302; G01N 27/36; G01N 27/304; G01N 27/31; G01N 27/40; G01N 27/30; G01N 27/301; G01N 27/401; G01N 27/403; G01N 31/164; G01N 31/166
See application file for complete search history.

(56) References Cited

U.S. PATENT DOCUMENTS 5,273,631 A 12/1993 Ohsawa et al.
6,964,734 B2 11/2005 Cha et al.
(Continued)

FOREIGN PATENT DOCUMENTS

EP 0740312 A2 10/1996

*Primary Examiner* — Gurpreet Kaur
(74) *Attorney, Agent, or Firm* — Standley Law Group LLP; Jeffrey S. Standley; Stephen L. Grant

(57) ABSTRACT

A cell and/or a measuring instrument are arranged for coulometric titration. The cell has first and second electrochemical half-cells, each of which is connected into a regulated circuit and each of which has an associated electrode. The second electrode (3) is immersed in an electrolyte (2) that is solid or solidified and fills a second housing (1). The second housing is closed, with charge and material exchange only possible through a diaphragm (4) that is disposed between the respective electrochemical half-cells. The electrolyte contains a first redox partner that, along with at least one second redox partner, is part of a redox system. The redox partners are selected to substantially suppress gas development inside the cell during operation. The first electrode and the second housing are disposed in a first housing so that at least the diaphragm and the first electrode are in contact with a sample during operation.

14 Claims, 4 Drawing Sheets

(56) References Cited

U.S. PATENT DOCUMENTS

| | | | |
|---|---|---|---|
| 8,475,639 B2 | 7/2013 | Srinivasan | |
| 2003/0209451 A1* | 11/2003 | Dineen | G01N 33/492 205/789 |
| 2004/0231984 A1* | 11/2004 | Lauks | B01L 3/5027 204/416 |
| 2006/0134442 A1* | 6/2006 | Sugiyama | C23C 18/2066 428/457 |
| 2009/0145777 A1* | 6/2009 | Srinivasan | G01N 31/164 205/788.5 |
| 2010/0135649 A1* | 6/2010 | Nakayama | G03B 9/02 396/261 |
| 2011/0089051 A1* | 4/2011 | Wang | B82Y 15/00 205/781 |
| 2011/0276281 A1* | 11/2011 | Wernet | G01F 23/241 702/55 |
| 2014/0151219 A1* | 6/2014 | Abulkibash | G01N 27/30 204/400 |
| 2015/0266849 A1* | 9/2015 | Paetz | C07D 319/12 549/274 |
| 2016/0131612 A1* | 5/2016 | Gilliam | G01N 27/38 436/80 |

* cited by examiner

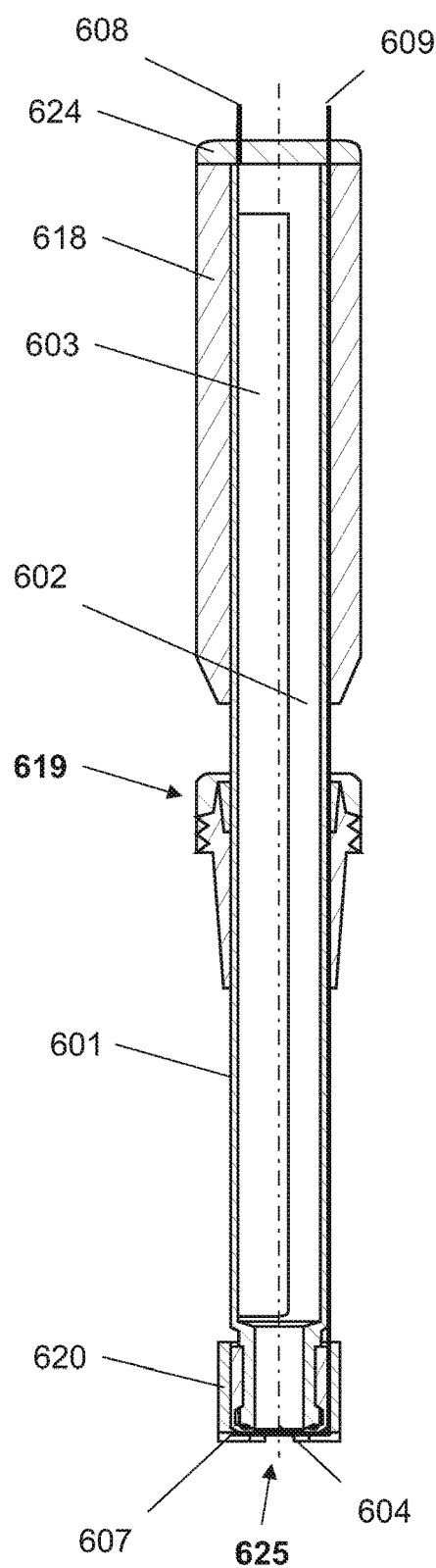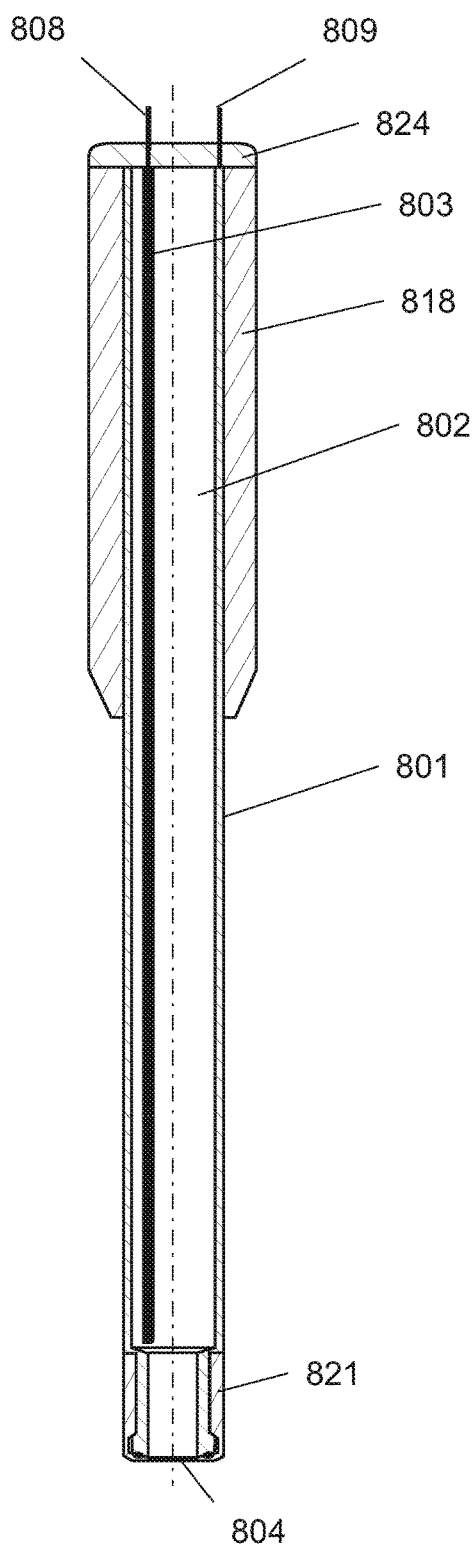
Fig. 6
Fig. 8

COULOMETRIC TITRATION CELL

CROSS-REFERENCE TO RELATED APPLICATIONS

This application is a by-pass continuation that claims the benefit of priority to PCT/EP2014/066953, filed on 7 Aug. 2014, which in turn claims the benefit of priority to EP 13180899.0, which was filed on 19 Aug. 2013. Both applications are incorporated by reference as if fully recited herein.

TECHNICAL FIELD

The invention relates to a coulometric titration cell for carrying out coulometric titrations as well as to a measuring instrument set-up with a coulometric titration cell of this type.

BACKGROUND

Volumetric titration is a routine method in many industrial laboratories for the quantitative determination of the quantity of a substance or an analyte in a fluid sample. Traditionally, a titration reagent is added from a burette to a sample, which latter is stirred, and the change, for example in the pH or the conductivity of the sample, is monitored using appropriate sensors. The unknown concentration or the quantity of the analyte in the sample can be determined with the aid of the volume of titration reagent consumed and the titer of the titration reagent by the end point or equivalence point of the titration and the stoichiometry of the reaction which has occurred. The term "titer" is used to describe the quotient of the actual concentration of a titration or measurement solution and the target concentration of that same solution. Thus, the titer is a factor in the characterization of normal solutions.

Nowadays, instead of manually operated burettes, automated titration devices are used; they are also known as titrators. Titrators comprise at least one automatic dosing element by means of which the titration reagent is added to a sample in predetermined increments or dynamically, at least one appropriate sensor, a control unit and a display unit. Furthermore, generally the titration reagent in a titrator is also fluid and it is necessary to inspect the titer of the titration reagent regularly and/or to prepare fresh titration reagent in order to avoid changes based on aging and/or contamination, because these lead to errors in the measurements.

In addition to volumetric titration, coulometric titration or coulometry is also known for the quantitative determination of the amount or concentration of an oxidizable or reducible compound. A coulometric titration cell comprises two electrochemical half-cells, wherein one electrochemical half-cell functions as the working electrode and the other electrochemical half-cell functions as a counter-electrode disposed in an electrolyte. In coulometry, the titration reagent is produced electrochemically at the working electrode during the titration and the electrical charge which is generated at the working electrode is determined. The reverse electrochemical process occurs at the counter-electrode, wherein the electrolyte within the electrochemical half-cell of the counter-electrode is consumed during the titration because of the reduction or oxidation of the substances contained at the counter-electrode. The two electrochemical half-cells of the coulometric titration cell can be separated from each other by a diaphragm which permits the transport of charge and material between the two electrochemical half-cells as a function of the type and polarity of the working electrode; transport through the diaphragm may be in one or both directions.

Depending on the configuration of the coulometric titration cells, acid or basic titrations may be carried out, for example, and the coulometric titration cell may be configured as a base or acid generator, whereby a base generator produces hydroxide ions ($OH^-$) for acid titration and an acid generator produces hydroxonium ions ($H_3O^+$) for base titration.

Published application WO 2009/076144 A1 discloses, for example, a coulometric titration cell with a platinum working electrode, a platinum counter-electrode and a multi-layered ion exchange membrane as the diaphragm. When a suitable electrolyte and a suitable ion exchange membrane are employed, the coulometric titration cell can be used for acid titration or for base titration depending on the polarization of the electrodes. As an example, for acid titration, an aqueous sodium hydroxide solution (NaOH) together with a cation exchange membrane may be employed.

Furthermore, for coulometric titrations, other substances may also be produced in situ, which then react with the analyte in the sample. If the sample contains iodide, then this can be reduced at the working electrode to iodine and then, for example, sulphur dioxide ($SO_2$) in the sample can be determined.

However, known coulometric titration cells suffer from the disadvantage that when carrying out the titration, gases are formed at the working electrode and/or the counter-electrode which have to be removed from the coulometric titration cell; also, they are often produced from precious metals and so are expensive to produce. In particular, the preparation of smaller and more compact coulometric titration cells has not previously been possible.

The objective of this invention is to provide a coulometric titration cell which is small and compact in design and which essentially does not produce any gases during operation.

SUMMARY

This objective is achieved by means of a coulometric titration cell for carrying out a coulometric titration of a sample, having a first electrochemical half-cell having a first electrode and having a second housing which comprises a second electrochemical half-cell with a second electrode and an electrolyte. The second electrode is immersed in the electrolyte. Furthermore, the coulometric titration cell comprises a redox system with a first and second redox partner, a diaphragm which is disposed between the first and second electrochemical half-cell and an electrical circuit into which the first and second electrochemical half-cells are connected. During operation, at least the diaphragm and the first electrode are in contact with the sample. The second housing is closed, so that charge and material transport is only possible via the diaphragm. Furthermore, the electrolyte, which is solid or solidified, contains the first redox partner. In addition, the first and second redox partners of the redox system are selected such that any gas development at the second electrode is essentially suppressed.

The coulometric titration cell in accordance with the invention is highly advantageous since, because of the selection of the first and second redox partners of the redox system, wherein the first redox partner is disposed in a solid or solidified electrolyte, during operation, any development of gas at the second electrode, which is immersed in the electrolyte, is essentially prevented. In this manner, it is possible to make the second housing, which surrounds the second electrochemical half-cell, particularly small and compact.

In particular, the diaphragm separates the second electrochemical half-cell from the first electrochemical half-cell as well as from the sample or the measuring medium during operation. Any charge and material exchange between the two electrochemical half-cells or between the sample and the second electrochemical half-cell can thus only occur via the diaphragm.

In a further embodiment, the second housing is disposed in a first housing in an interchangeable manner, so that the second electrochemical half-cell together with the second housing can easily be changed when the electrolyte contained in it is spent. The first housing can also comprise the first electrochemical half-cell.

The development of gas inside the coulometric titration cell can also be substantially reduced or even completely suppressed by selecting a suitable redox system. The redox system may comprise one of the following combinations of substances and/or compounds of these substances as the first and second redox partner: iodine/iodide, iron (II/III) cyanide compounds ($Fe(CN)_6^{3-/4-}$), zinc/zinc (II) compounds.

A zinc/zinc (II) redox system may comprise a zinc complex compound in the coulometric titration cell in accordance with the invention as the first redox partner, such as $Zn[(NH_3)_2(H_2O)_2]^{2+}$ as a chloride, nitrate or sulphate compound, for example. An example of the second redox partner is a zinc sacrificial electrode as the second electrode. In a further embodiment, the second redox partner may be in the form of zinc powder which is added to the solid electrolyte. To increase the conductivity, an electrically conductive compound may be added to the electrolyte as an additive, for example graphite or conductive salts (for example $K_2SO_4$, $Na_2O_3SCH_3$, $Na_2O_3SCF_3$).

Preferably, the electrolyte or the second electrode comprises the second redox partner. Both redox partners may thus be present in the electrolytes. In a further embodiment, the first redox partner is in the electrolyte and the second redox partner is contained in the second electrode which, for example, may be produced by using a sacrificial electrode as the second electrode.

Preferably, the coulometric titration cell comprises a reversible redox system so that depending on the circuitry, the first electrode can be connected and can be employed as anode or cathode. A reversible redox system is configured such that the chemical equilibrium between the two redox partners can be displaced in one or the other direction by connecting the first electrode as the anode or as the cathode. With a reversible redox system, at least to a certain extent, both acid and base titrations are possible with the same coulometric titration cell without having to change the electrolyte or the diaphragm.

Displacing the chemical equilibrium between the two redox partners means that at least partial regeneration of the coulometric titration cell is possible and/or that the same coulometric titration cell can be used in a flexible manner as either an acid or base generator.

In contrast to the known prior art, the first electrode and the second electrode are preferably free of noble metals. The first electrode may comprise a metal, a metallic compound or mixtures thereof, wherein the metal is preferably selected from the group which comprises iron, chromium, molybdenum, nickel and/or titanium.

The second electrode may also comprise a metal, a metallic compound or mixtures thereof, wherein the metal is preferably selected from the group which comprises iron, chromium, molybdenum, titanium, nickel and/or zinc. In particular, a second electrode containing zinc may, for example, also be used as a sacrificial electrode.

In a further embodiment, the first and/or second electrode may completely or partially consist of a glass carbon material or an electrically conductive polymer.

In a further embodiment, the first or second housing may contain an electrically conductive polymer or consist of an electrically conductive polymer which, because of its properties, can itself be connected into the electrical circuit of the coulometric titration cell, so that the first or second housing can act as the first electrode. In this manner, it is possible to produce the coulometric titration cell in a particularly small, compact and inexpensive manner, since using the first or second housing as the first electrode means that a separate first electrode can be dispensed with.

Particularly suitable electrically conductive polymers for use in a coulometric titration cell are polymers which contain one or more additives in order to increase the electrical conductivity. Examples of suitable additives are graphite, metallic particles, metallic compounds and/or carbon nanotubes. The additive is preferably added to the polymer in an admixture of approximately 20% to approximately 35%.

An example of a solid electrolyte is an aqueous solution of the first redox partner or the first and second redox partner to which, for example, approximately 10% to approximately 40% of silica gel is added in order to bind the water contained therein. In addition to silica gel, phyllosilicates or tectosilicates such as zeolites, or cellulose compounds such as hydroxyethylene cellulose may be added as a binder for the water.

If, for example, a $Zn/Zn^{2+}$ redox system is used, then $Zn^{2+}$ is formed in the electrolyte during the titration, which can be bound with a suitable complexing agent or ion exchanger. The complexing agent is also added to the electrolyte. Examples of the complexing agent or ion exchanger are zeolites or clay minerals or silicates which act in a similar manner.

If, for example, an $I_2/I_3^-$ or $Fe(CN)_6^{3-/4-}$ redox system is employed, then the use of further complexing agents or ion exchangers can be dispensed with, since in this case the first and second redox partners are themselves complexing agents. These redox systems can also be employed together with a solid or solidified electrolyte.

Instead of solid electrolytes, solidified electrolytes may also be used, such as hydrogels, which contain at least the first redox partner. A hydrogel electrolyte for a coulometric titration cell may, for example, be produced by transforming an aqueous $ZnX_2$ solution into a hydrogel, wherein in particular, X comprises one of the following anions: $Cl^-$, $SO_4^{2-}$, $CH_3SO_3^-$, triflate: $—CF_3SO_3^-$ (triflate), p-tol $SO_3^-$ (tosylate). In this regard, linear polymer chains such as poly-N-vinylformamide, for example, or even cross-linked polymer chains such as a copolymer formed from glycerine methacrylate and N,N'-bis-acrylamide, for example, may be employed. In order to guarantee a sufficiently high ion transport in the hydrogel, it is important that the viscosity of the hydrogels used is adapted or adjusted. A suitable viscosity may be obtained by using approximately 10% by weight to approximately 30% by weight of monomer.

In addition, hydrogels have an advantage as regards production techniques because they are introduced into the second housing in the liquid form and thus may be polymerized directly, i.e. in situ, and thus solidified therein.

Depending on the embodiment, the diaphragm which is disposed between the first and second electrochemical half-cell can, permit charge and material transport between the first and second electrochemical half-cell which occurs bi-directionally or uni-directionally only from the second to the first electrochemical half-cell. Advantageously, the diaphragm essentially consists of a porous ceramic, a porous glass and/or an ion-selective membrane.

The diaphragm may be formed as an anion exchange membrane or a cation exchange membrane; the type and form of the diaphragm is a function of the use of the coulometric titration cell as an acid or base generator as well as of the redox system employed.

Furthermore, an inert salt may be added to the sample which does not change the sample chemically, and thus is chemically inert as regards the sample. Examples of inert salts of this type are potassium ($K_2SO_4$) or potassium nitrate ($KNO_3$). Adding an inert salt can increase the conductivity of the sample, which is usually present as a fluid, for example as a solution or suspension. Increasing the conductivity of the sample allows a coulometric titration to be carried out with a lower voltage applied between the first and second electrodes, since by adding the inert salt, the ion mobility is increased and the charge balance between the sample and the coulometric titration cell is improved.

Furthermore, the second electrochemical half-cell of the coulometric titration cell may have a chemical or physical diffusion trap which acts to prevent material transport from the second electrochemical half-cell into the sample or the measuring medium. Using diffusion or ion traps to maintain the functionality of coulometric titration cells is known in principle.

In a further aspect, the invention concerns the provision of a measuring instrument set-up for carrying out a coulometric titration on a sample with a coulometric titration cell having the features described above. In this regard, the measuring instrument set-up comprises a container which accommodates the sample during operation, a sensor to acquire the end or equivalence point of the titration, and a control and/or display unit. The coulometric titration cell is in contact with the sample via at least the diaphragm and the first electrode during operation. The second housing of the coulometric titration cell is closed so that any charge and material exchange is only possible via the diaphragm. The electrolyte is solid or solidified and contains a first redox partner. In addition, the first and second redox partners of the redox system are selected such that during operation, gas development at the second electrode is substantially suppressed.

The sensor in a measuring instrument set-up in accordance with the invention may, for example, be an ion-selective, potentiometric or conductivity sensor by means of which at least one parameter of the sample is acquired during the titration until the end or equivalence point is reached.

BRIEF DESCRIPTION OF THE DRAWINGS

Various embodiments of a coulometric titration cell in accordance with the invention will now be described in more detail with the aid of the accompanying drawings, in which identical elements are provided with identical or similar reference numerals, and in which:

FIG. 6 shows a section through a further coulometric titration cell, with a front end-mounted diaphragm;

FIG. 8 is a section through a further coulometric titration cell with a front mounted diaphragm and a second housing formed as the first electrode.

DETAILED DESCRIPTION OF THE DRAWINGS

Figure 1:
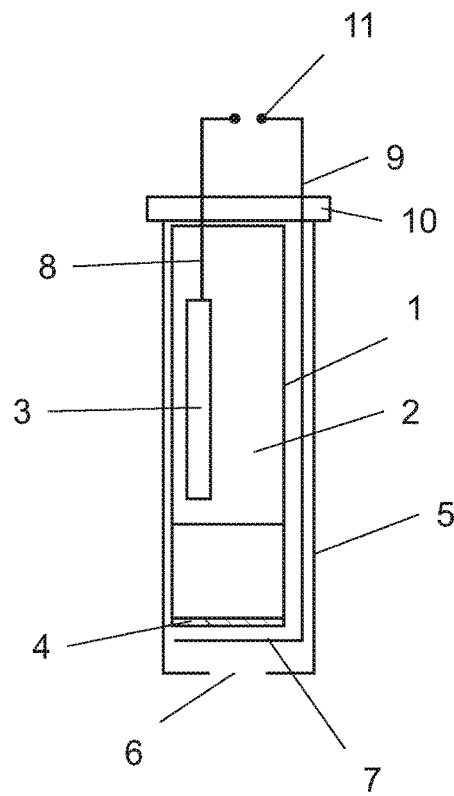
FIG. 1 shows a diagrammatic representation of a coulometric titration cell, in which a second housing is disposed in an interchangeable manner in a first housing.

FIG. 1 shows a diagrammatic representation of a coulometric titration cell in accordance with the invention with a second housing 1, which is filled with a solid or solidified electrolyte 2 in which a second electrode 3 is immersed. The second housing 1 is closed. Any charge and material transport is only possible through a diaphragm 4 which is disposed in the first housing in a manner such that during operation, it is in contact with a sample to be titrated. An electrical connection 8 for the second electrode 3 leads out of the second housing 1.

Furthermore, the coulometric titration cell shown in FIG. 1 comprises a first housing 5 which has an opening 6 for contact with the sample. A first electrode 7 as well as the second housing 1 are disposed in the first housing 5. The first housing 5 is closed with a cover 10 in a manner such that the second housing 1 and the components contained therein can be changed. In addition, electrical contacts 8, 9 lead through the cover 10 in this embodiment via which the first and second electrodes 3, 7 are connected into a regulated circuit 11, shown here in a highly simplified manner.

Figure 2:
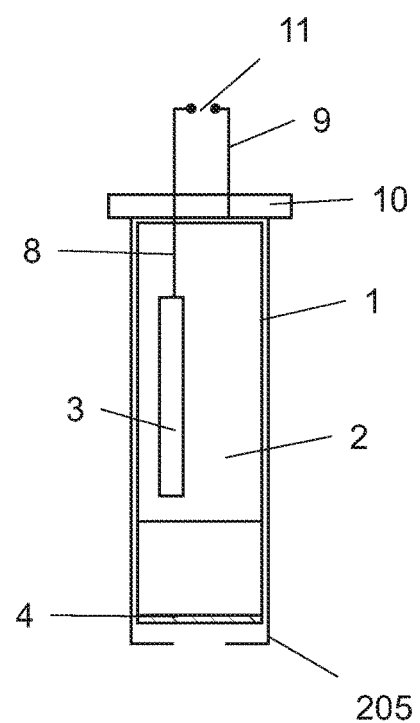
FIG. 2 shows a diagrammatic representation of a further coulometric titration cell, in which the first housing is configured as the first electrode.

FIG. 2 shows a further embodiment of a coulometric titration cell in accordance with the invention which is essentially identical to the coulometric titration cell described with respect to FIG. 1. However, in this embodiment, there is no separate first electrode disposed in the first housing 205, but the first housing 205 itself constitutes the first electrode. In this manner, the first housing 205 can act as the first electrode, and so it at least partially consists of an electrically conductive polymer and is connected into the circuit 11 via an electrical connection 9, as can be seen in FIG. 2.

Figure 3:
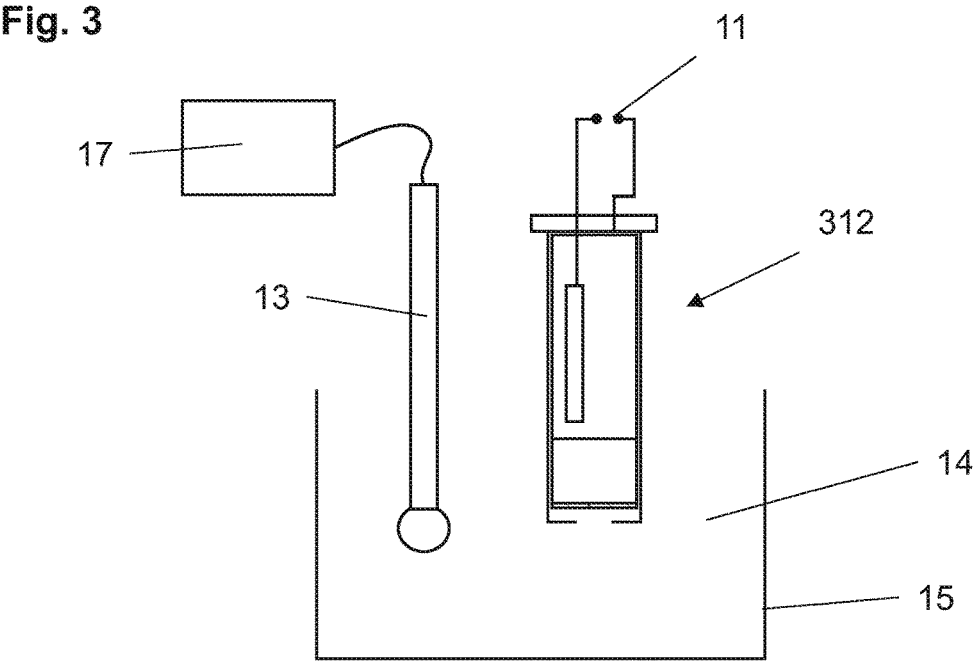
FIG. 3 shows a diagrammatic representation of a measuring instrument set-up, with a coulometric titration cell in accordance with FIG. 2 and a sensor.

FIG. 3 shows a diagrammatic representation of a measuring instrument set-up with a coulometric titration cell 312 and a sensor 13. The coulometric titration cell 312 corresponds to the embodiment shown in FIG. 2, wherein a coulometric titration cell in accordance with FIG. 1 can also be used. Both the sensor 13 and the coulometric titration cell 312 are immersed in a sample 14 on which the titrimetric determination or a coulometric titration is to be carried out. The sample 14 or the measuring medium is disposed in a suitable container 15 during the titration. As a rule, the sample 14 is a fluid, for example a solution or a suspension.

In order to increase its conductivity, an inert salt may be added to the sample 14. Herein, salts are described as inert salts when they are chemically inert towards the sample and do not change it chemically. Examples of inert salts of this type include potassium sulfate ($K_2SO_4$) or potassium nitrate ($KNO_3$). Increasing the conductivity of the sample 14 enables the coulometric titration to be carried out at a lower voltage which is applied between the first and second electrodes, since adding the inert salt increases the ion mobility and thus improves the charge balance between the sample and the coulometric titration cell. As an example, the sensor 13 may be an ion-selective, potentiometric or conductivity sensor. Using the sensor 13, an appropriate parameter of the sample 14 is acquired during the titration until the end point or equivalence point of the coulometric titration is reached, and is illustrated here by a control and/or display unit 17.

Figure 4:
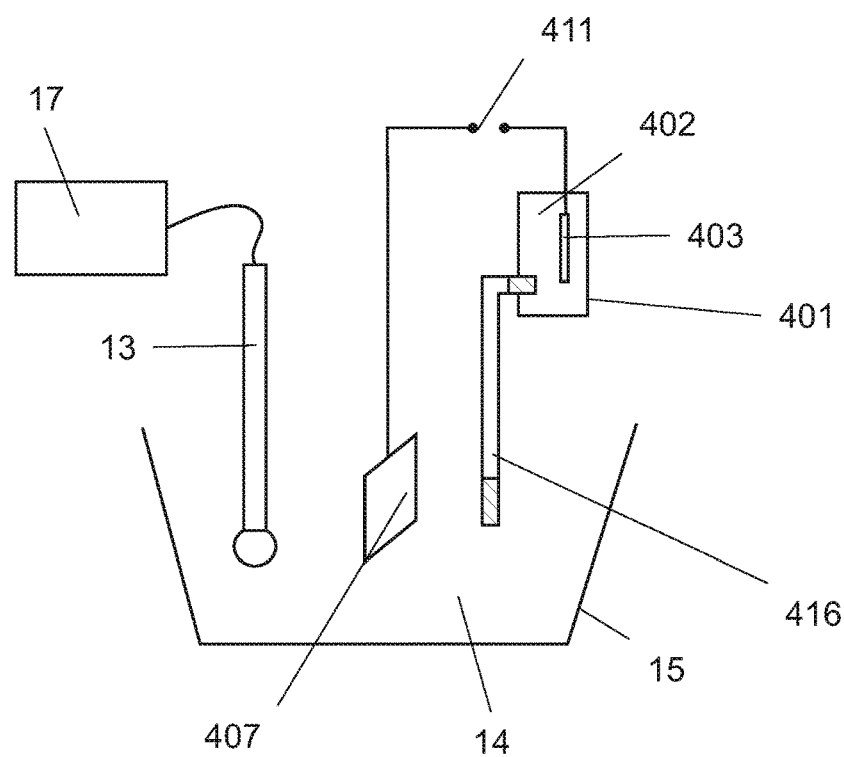
FIG. 4 shows a diagrammatic representation of a further measuring instrument set-up, with a coulometric titration cell in accordance with the invention and a sensor.

FIG. 4 diagrammatically shows a further measuring instrument set-up with a sensor 13 and a coulometric titration cell in a further embodiment. This coulometric titration cell comprises a second housing 401 in which a second electrode 403 is disposed. The second electrode 403 is connected into a circuit 411 and the second housing 401 has an electrolyte bridge 416 which contains a diaphragm or is configured as a diaphragm. During operation, the electrolyte bridge 416 is in contact with a sample 14 which is in a container 15. Furthermore, during operation a first electrode 407 is immersed in the sample 14 which also is connected into the circuit 411 and a sensor 13 which is connected with a suitable control and/or display unit 17. During operation, the electrolyte bridge 416 constitutes a contact between the second electrochemical half-cell with the second electrode 403 and the first electrochemical half-cell with the first electrode 407, so that charge and material transport between the two electrochemical half-cells can occur.

Figure 5:
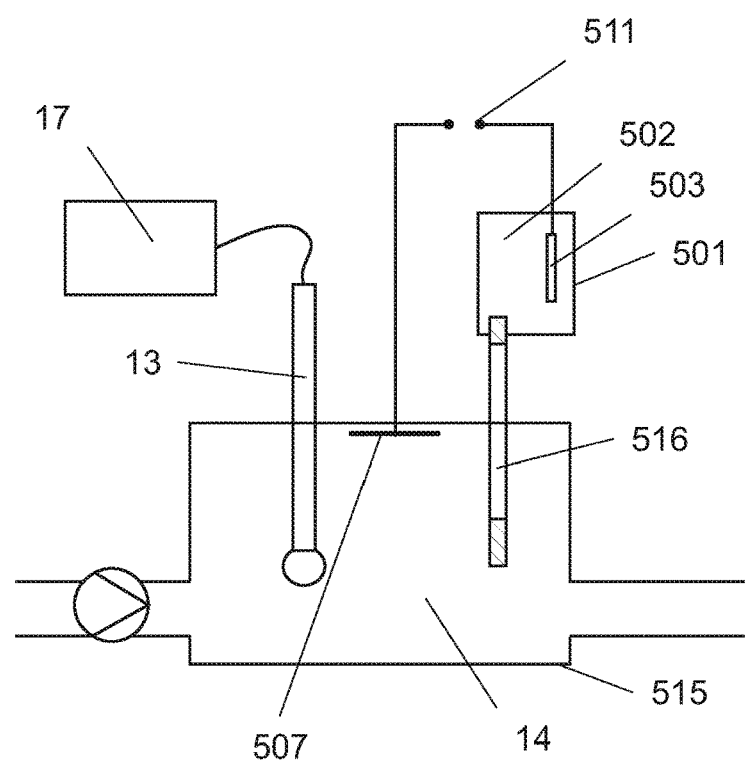
FIG. 5 shows a diagrammatic representation of a flow measuring instrument set-up, with a coulometric titration cell in accordance with the invention and a sensor.

FIG. 5 diagrammatically shows a flow measuring instrument set-up with a sensor 13 and a coulometric titration cell. A sample 14 flows through a flow cell 515 in which the sensor 13 and a first electrode 507 are disposed. The sensor 13 is in turn connected to a control and/or display unit 17. The first electrode 507 and a second electrode 503 are connected into a circuit 511. The second electrode 503 is disposed in a closed housing 501 and is immersed in an electrolyte 502 disposed therein. The second electrochemical half-cell with the second electrode 503 is connected with the first electrochemical half-cell via an electrolyte bridge 516 which, as described in FIG. 4, comprises a diaphragm. The electrolyte bridge 516 is configured in a manner such that during operation of the coulometric titration cell, charge and also material transport is possible between the second and first electrochemical half-cells.

Because of the spatial separation of the first and second electrochemical half-cells as can be seen in FIGS. 4 and 5, for example, a particularly small and compact coulometric titration cell can be produced.

Figure 7:
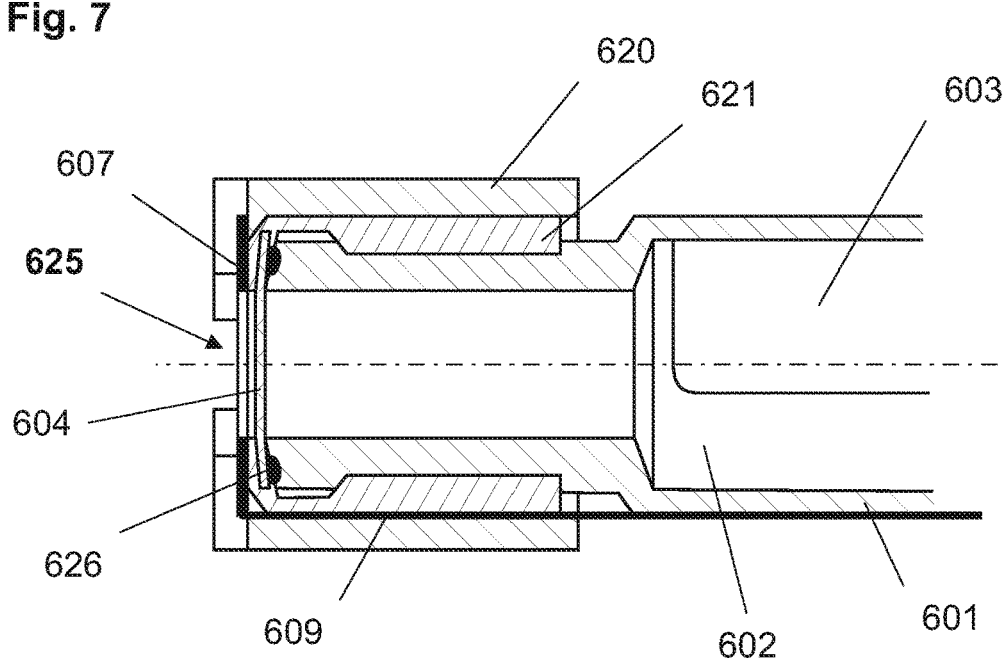
FIG. 7 is a partial sectional view of the coulometric titration cell of FIG. 6.

FIGS. 6 to 8 show two further embodiments of a coulometric titration cell in accordance with the invention, wherein FIG. 7 is a partial representation of FIG. 6.

The coulometric titration cell shown in FIGS. 6 and 7 comprises a longitudinal tubular second housing 601 which is filled with a solid or solidified electrolyte 602. A second electrode 603 is immersed in the electrolyte 602. The second electrode 603 in this embodiment is a thin sheet or a thin plate formed from a suitable electrode material which is disposed on the inner wall of the housing 601.

The end of the housing 601 facing away from the sample or the measuring medium during operation is closed with a cover 624 which also is the closing element for a gripping element 618. As an example, the cover 624 may be removed to top up or change the electrolyte 602. Advantageously, the cover 602 is releasably connected to the gripping element 618 and the second housing 601.

The front end of the second housing 601 which is immersed in a measuring medium or a sample during operation is closed by means of a diaphragm 604 which is fixed to the second housing 601 by means of a retaining element 621. To prevent the sample from penetrating into the second housing 601, a seal 626 is disposed between the diaphragm 607 and the second housing 601, in this case an O-ring. On the sample side, a first electrode 607 is disposed in front of the diaphragm 604; in this embodiment, the first electrode is annular in shape so that during operation, the sample can come into contact with the diaphragm 604 via the recess in the annular first electrode 607.

The front end of the second housing 601 is enclosed by a first housing 620, leaving an opening 625. During operation, the opening 625 ensures contact between the diaphragm 604 and the sample into which the front end of the coulometric titration cell is immersed. In addition, the first electrode 607 is disposed in the first housing 620.

Both the first and the second electrodes 603, 607 are connected into a circuit via electrical connections 608, 609 which are fed through the cover 624 (see FIGS. 1 to 5).

The sensor 13 shown in FIGS. 3 to 5 may, for example, be an ion-selective, potentiometric or conductivity sensor. At least one parameter of the sample 14 is acquired with the sensor 13 during titration until the end or equivalence point is reached, as indicated in the figures by the control and/or display unit 17. This control and/or display unit 17 may also regulate the tension or current between the first and second electrodes, analyze the parameters which have been acquired, determine the result of the coulometric titration and display it. The control and/or display unit 17 may be configured as separate components or as a combined component.

Furthermore, FIG. 6 shows an adapter 619 which serves to insert the coulometric titration cell into a holder of a titrator, for example.

FIG. 8 shows a further embodiment of a coulometric titration cell with a front end diaphragm 804 which seals a longitudinal tubular second housing 801. As already shown in FIGS. 6 and 7, a seal is disposed between the diaphragm 804 and the second housing 801. The diaphragm 804 is retained on or fixed to the second housing 801 by means of a retaining element 821.

The second housing 801 is filled with a solid or solidified electrolyte 802 into which a rod-shaped second electrode (in this embodiment) 803 is immersed. The end of the second housing 801 opposite to the sample during operation is partially surrounded by a gripping element 818 and is releasably closed with a cover 824, as already described with respect to FIGS. 6 and 7. Electrical connections 808, 809 for connecting the second electrode 803 and a first electrode are fed through the cover 724. The first electrode in this embodiment is formed by the second housing 801 which comprises an electrically conductive polymer or an electrically conductive layer. The second housing 801 is connected with the electrical connection 809.

Figure 9:
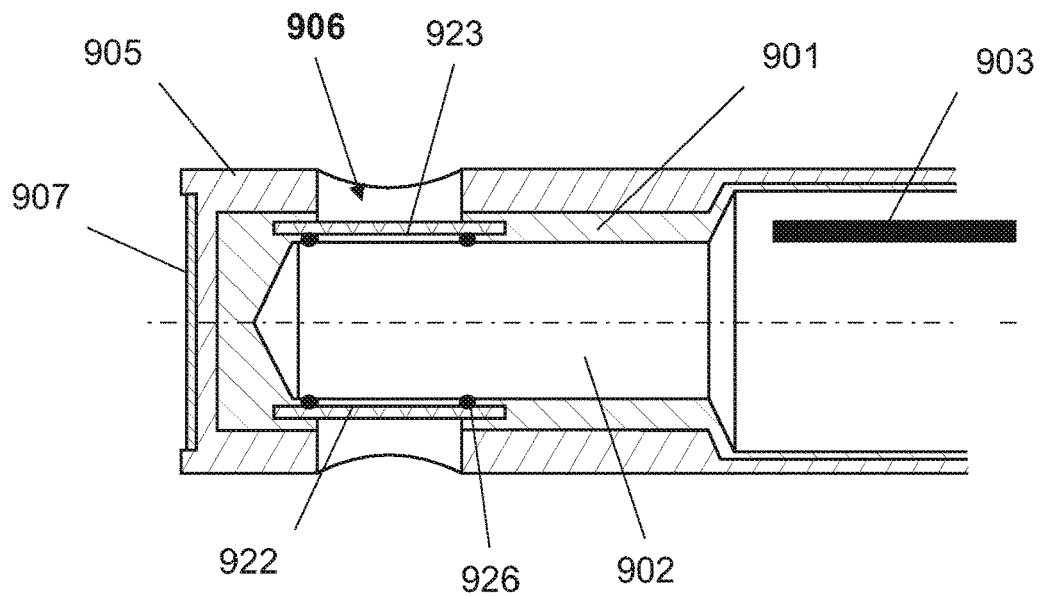
FIG. 9 is a partial representation of a further coulometric titration cell with two laterally disposed diaphragms and an interchangeable second housing.

FIG. 9 shows a partial sectional representation of a further coulometric titration cell with at least two laterally disposed diaphragms 922, 923.

The coulometric titration cell again comprises a longitudinal and essentially tubular second housing 901 which is disposed in a first housing 905 in an interchangeable manner. The second housing 901 is filled with a solid or solidified electrolyte 902 and is sealed against a sample during operation by means of at least two laterally disposed diaphragms 922, 923. The diaphragms 922, 923 are sealed by two seals 926 so that during operation, the sample is only in contact with the second electrochemical half-cell via the diaphragms 922, 923. Furthermore, a rod-shaped second electrode 903 is immersed in the electrolyte 902, as already described in relation to FIG. 8.

A first electrode 907 is applied to the front end of the first housing 905 facing the measuring medium; here, it is in the form of a flat disk embedded in the first housing 905. Furthermore, the first housing 905 comprises at least two lateral openings 906 which are disposed such that during operation, the diaphragms 922, 923 and the first electrode 907 can come into contact with the sample.

The first and second electrodes 903, 907 are also connected via suitable electrical connections into the circuit which is not shown in this partial representation.

Although the invention has been described with respect to specific exemplary embodiments, clearly many other variations may be generated with knowledge of the present invention; for example, the features of the individual exemplary embodiments may be combined together and/or individual functional elements of the exemplary embodiments may be interchanged. In particular, the exemplary embodiments shown in FIGS. 6 to 9 may be provided with or may not be provided with an interchangeable second housing; in addition, the first electrode may be configured as a rod, sheet or plate. A coulometric titration cell in accordance with the described exemplary embodiments may be used in one of the measuring instrument set-ups described for carrying out a coulometric titration. Equally, the coulometric titration cells of FIGS. 6 to 8 may be formed with or without an adapter. In this respect, the adapter may be configured in various forms which are suitable for use in an automated titration device or on a suitable rack.

What is claimed is:

1. A cell for carrying out a coulometric titration of a sample, comprising:
   a first electrochemical half-cell with a first electrode;
   a second housing, comprising:
      a second electrochemical half-cell with a second electrode;
      an electrolyte, in which the second electrode is immersed, the electrolyte being solidified as a hydrogel; and
      at least one diaphragm, disposed between the first and second electrochemical half-cell, the second housing being otherwise closed so that charge and material exchange occurs only via the diaphragm;
   a redox system with at least one first and second redox partner, the first redox partner contained in the electrolyte and the respective second redox partner contained in the second electrode, selected to substantially suppress gas development at the second electrode during operation; and
   a circuit into which the first and second electrochemical half-cells are connected, such that, during operation, the at least one diaphragm and the first electrode are in contact with the sample.

2. The coulometric titration cell of claim 1, further comprising:
   a first housing, in which the second housing is interchangeably disposed.

3. The coulometric titration cell of claim 2, wherein:
   the redox system comprises one of the following combinations of substances and/or compounds of these substances: iodine/iodide, iron (II/III) cyanide compounds, and zinc/zinc (II) compounds.

4. The coulometric titration cell of claim 1, wherein:
   the redox system is a reversible redox system and the second electrode acts as anode or cathode.

5. The coulometric titration cell of claim 1, wherein:
   the first electrode comprises one of the following metals, a metallic compound and/or a mixture thereof: stainless steel, chromium, molybdenum, nickel and/or titanium.

6. The coulometric titration cell of claim 1, wherein:
   the second electrode comprises one of the following metals, a metallic compound and/or a mixture thereof: stainless steel, chromium, molybdenum, nickel, titanium and/or zinc.

7. The coulometric titration cell of claim 1, wherein:
   at least one of the first electrode and/or the second electrode consists entirely or partially of a glass carbon material or an electrically conductive polymer.

8. The coulometric titration cell of claim 2, wherein:
   at least one of the first housing and the second housing comprises an electrically conductive polymer and acts as the first electrode.

9. The coulometric titration cell of claim 8, wherein:
   the electrically conductive polymer comprises carbon nanotubes.

10. The coulometric titration cell of claim 1, wherein:
    the diaphragm comprises a porous ceramic, a porous glass and/or an ion-selective membrane.

11. The coulometric titration cell of claim 1, wherein:
    the diaphragm is an anion exchange membrane.

12. The coulometric titration cell of claim 1, wherein:
    the diaphragm is a cation exchange membrane.

13. A measuring instrument for carrying out a coulometric titration of a sample, comprising:
    a cell for coulometric titration, according to claim 1;
    a container, in which the sample is disposed, such that the cell is in contact with the sample via at least the diaphragm and the first electrode during operation;
    a sensor, arranged in the sample for capturing an end or equivalence point of the titration; and
    a control and/or display unit, in communication with the sensor.

14. The measuring instrument of claim 13, wherein:
    the sensor is an ion-selective, potentiometric or conductivity sensor with which, during the titration, at least one parameter of the sample is acquired until the end or equivalence point is reached.

* * * * *